United States Patent [19]

Witzeman

[11] Patent Number: 5,117,060
[45] Date of Patent: May 26, 1992

[54] PROCESS FOR THE PREPARATION OF KETOXIMES

[75] Inventor: Jonathan S. Witzeman, Kingsport, Tenn.

[73] Assignee: Eastman Kodak Company, Rochester, N.Y.

[21] Appl. No.: 712,820

[22] Filed: Jun. 10, 1991

Related U.S. Application Data

[63] Continuation-in-part of Ser. No. 7,534,585, Jun. 6, 1990, abandoned.

[51] Int. Cl.$^5$ ............................................. C07C 249/08
[52] U.S. Cl. ...................... 564/259; 528/44; 528/45
[58] Field of Search ...................... 528/44, 45; 504/259

[56] References Cited

U.S. PATENT DOCUMENTS

| | | | |
|---|---|---|---|
| 4,085,551 | 10/1977 | Pancindiken et al. | 528/44 |
| 4,128,580 | 12/1978 | Matsumoto et al. | 564/259 |
| 4,150,211 | 4/1979 | Muller et al. | 528/45 |
| 4,507,248 | 3/1985 | Mathew et al. | 564/259 |

*Primary Examiner*—James H. Reamer
*Attorney, Agent, or Firm*—J. Frederick Thomsen; William P. Heath, Jr.

[57] ABSTRACT

Disclosed is an improved process for the preparation of ketoximes, especially ketoximes derived from branched chain ketones, wherein a ketone is reacted with a hydroxylamine salt in the presence of an alkanol, a heterogeneous base and up to about 5 weight percent, based on the weight of the ketone and alkanol, water.

15 Claims, No Drawings

PROCESS FOR THE PREPARATION OF KETOXIMES

This application is a continuation-in-part of copending application Ser. No. 07/534,585 filed Jun. 6, 1990, now abandoned.

This invention pertains to the preparation of ketoximes, especially hindered or branched chain ketoximes. More particularly, this invention pertains to a process for the preparation of ketoximes by the reaction of a ketone with a hydroxylamine salt in the presence of a heterogenous carbonate base. This invention further pertains to a process for the preparation of adducts of ketoximes, prepared as described herein, and polyisocyanate compounds.

The reluctance of branched chain ketones to react with hydroxyl amine is well known in the art. The rate of oximation of over 200 ketones was determined by Kletzke, J. Chem. Eng. Data, 1973, 18, 93 and J. Org. Chem., 1964, 29, 1363, and shown to be dependent on a variety of structural factors. Kletzke's work showed that oximation of diisobutyl ketone (2,6-dimethyl-4-heptanone) is about 600 times slower than the corresponding reaction of 2-pentanone, while diisopropyl ketone (2,4-dimethyl-3-pentanone) is fully 2600 times slower. The preparation of oximes typically involves addition of an aqueous base to a bi-phasic mixture of ketone and aqueous hydroxylamine using a co-solvent such as ethanol as is disclosed by Sandler and Karo, "Organic Functional Group Preparations", Vol. 3, pp. 372-381, Academic Press, New York, 1972. Among the bases used are aqueous solutions of sodium hydroxide (Buck et al, Org. Syn. Coll. Vol. II, p. 622; Schoenewaldt et al, J. Org. Chem. 1968, 33, 4270) or sodium carbonate (Bousquet, Org. Syn. Coll. Vol. II, p. 313). Another method of preparation involves the portion-wise addition of powdered sodium hydroxide to a reaction mixture which contains both organic and aqueous phases (Lachman, Org. Syn. Coll. Vol. II, p. 70).

Autrey et al, J. Am. Chem. Soc. 1968, 90, 4924, have reported the preparation of the ketoxime of tetralone by the addition of powdered sodium hydroxide to a reaction mixture containing alcohol, hydroxylamine hydrochloride and the ketone in the absence of water. Another method, reported by Pearson et al, J. Org. Chem. 1963, 28, 1557, for the preparation of highly hindered oximes involves the reaction of a ketone and hydroxylamine source with a mixture of 2-methyl-2-butanol/potassium 2-methyl-2-butoxide at room temperature over several months time. Pearson et al note that the reaction can not be accelerated by heating due to competing decomposition of the hydroxyl amine. The reaction of hindered ketones with hydroxylamine at 9500 atmospheres pressure has been reported by Jones et al, J. Am. Chem. Soc. 1959, 81, 2151.

U.S. Pat. No. 4,507,248 discloses the synthesis of ketoximes using a preformed hydroxylamine/alkanol solution. The disclosed process requires a plurality of process steps which include (1) preparing a concentrated solution of an alkali metal hydroxide in methanol or ethanol, (2) adding the step (1) solution to a mixture of a hydroxylamine salt in an alkanol to form a homogeneous solution of hydroxylamine, (3) the homogeneous solution of hydroxylamine with a ketone, and (4) adjusting the pH, either before or after the hydroxylamine-ketone reaction. The multi-step process further requires the use of very low temperatures, e.g., 5°-10° C. are used in the examples, in the preparation of the homogeneous solution of hydroxylamine in the second step and also in the third step if the pH is not adjusted between the second and third steps. According to this patent, the use of higher temperatures gives significantly lower yields. The maintenance of such low temperatures is a serious disadvantage when operating on a commercial scale, especially since the conversion of a hydroxylamine salt to free hydroxylamine is an exothermic reaction. Furthermore, only certain combinations of particular bases and alcohols may be used.

The process of U.S. Pat. No. 4,507,248 requires, in the hydroxylamine ketone reaction, either burdensome and difficult to-achieve cooling of the reaction mixture or a pH adjustment prior to the hydroxylamine-ketone reaction. Apparently, the cooling/pH adjustment is essential to avoid side reactions of the ketone, e.g., aldol condensation which is known to be catalyzed by strong base.

U.S. Pat. No. 4,128,580 discloses a process for making an oxime of a specific ketone, 1,3-dichloroacetone, by reacting 1,3-dichloropropanone with a hydroxylamine salt at a low pH, i.e., a pH of 2 or less. The homogeneous process is performed in the presence of water or a mixture of water and a hydrocarbon. This pH regime is maintained by using combinations of a strong acid such as hydrochloric acid and small amounts of materials capable of buffering the solution such as pyridine or calcium carbonate. These conditions are very specific to this highly reactive ketone, due to its propensity to undergo a variety of undesirable reactions such as condensation.

I have discovered that ketoximes, especially oximes of branched chain ketones, can be prepared in good yields at satisfactory rates by contacting a ketone with a hydroxylamine salt in the presence of an alkanol solvent, a heterogeneous carbonate base and up to about 5 weight percent, based on the weight of the ketone and alkanol, water. The presence of water in the reaction mixture has been found to enhance reaction rates. The presence of such minor amounts of water is particularly advantageous in the practice of the process on an industrial scale since the water/alkanol mixture is less flammable than the anhydrous alkanol. The products obtained from this embodiment of my invention are of adequate purity and low enough color to be used in subsequent reactions after a solvent stripping operation. The process, in general, also is advantageous in that it may be carried out on a commercial scale in a single vessel and no dramatic temperature increases (exotherms), which are especially troublesome in commercial operations, occur during the practice of the process.

The ketoxime products of my novel process are particularly useful in the manufacture of blocked isocyanate compounds which are used extensively in thermosetting coating formulations, particularly powder coating compositions. Ketoximes also are used as chemical intermediates for a variety of agrichemical and pharmaceutical applications, as antiskinning aids in paints and in silicone sealants.

The process provided by this invention may be used to prepare the oximes of dialkyl ketones (alkanones) having about 5 to 20 carbon atoms. However, the advantages inherent in the process render the process particularly useful for the preparation of oximes of branched chain (hindered) alkanones having about 7 to 20 carbon atoms wherein the branching occurs at both carbon atoms $\alpha$ or $\beta$ relative to the ketone carbonyl.

Such branched chain ketones may be characterized by the formula

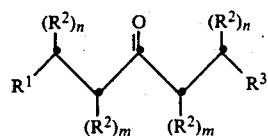

wherein $R^1$ and $R^3$ are independently selected from hydrogen and alkyl of up to about 6 carbon atoms; each $R^2$ is hydrogen or alkyl of up to about 3 carbon atoms, especially methyl; m and n each is 0 or 1; and the sum of $m+n=2$, provided that the alkanones are branched chain, e.g., when $R^1=R^2=$hydrogen, each $m=1$. Examples of such alkanones include 2,4-dimethyl-3-pentanone (diisopropyl ketone) and 2,6-dimethyl-4-heptanone (diisobutyl ketone).

The alkanol reaction medium consists of 1 or more alkanols of up to about 4 carbon atoms with ethanol and 1- and 2-propanol being particularly suitable. The amount of alkanol is not a critical element of my invention and can be varied substantially depending, for example, on the materials and equipment used in the process. Typically, the amount of alkanol used will give an alkanol:ketone weight ratio in the range of about 0.3:1 to 3:1, preferably about 0.6:1 to 2.2:1. As noted above, the alkanol solvent may contain, and preferably contains, up to about 5 weight percent, based on the weight of the alkanol and ketone, water, e.g., from about 3 to 5 weight percent.

The hydroxylamine salt used may be any compound which provides hydroxylamine in the practice of the process. Hydroxylamine hydrochloride and hydroxylamine sulfate are readily available salts and, therefore, represent the preferred hydroxylamine salts. The amount of the hydroxylamine salt employed may vary considerably, depending on various factors such as the amount of alkanol present, the equipment utilized, etc. To achieve reasonable production rates, the hydroxylamine salt normally is used in an amount of about 0.6:1 to 1.5:1, preferably about 0.8:1 to 1.1:1, equivalents of hydroxylamine salt per mole of ketone reactant.

The carbonate base compound required by the process of the present invention may be any compound which will convert the hydroxylamine salt to hydroxylamine under the conditions and in the presence of the alkanols and ketones employed in the process. Examples of such carbonate base compounds include the alkali and alkaline earth carbonates and bicarbonates. The alkali bicarbonates and, particularly, carbonates, especially sodium and potassium carbonate, are the preferred carbonate base compounds. These carbonate compounds typically are used in an amount of about 0.8 to 2, preferably about 1.0 to 1.6, equivalents of carbonate base compound per equivalent of the hydroxylamine salt.

The process provided herein preferably is carried out at a temperature of about 65° C. up to the boiling point of the reaction mixture, e.g., up to about 110° C. Pressure is not an important feature of the process and thus the process may be carried out at atmospheric pressure or moderately elevated pressures, e.g., to achieve a reaction temperature higher than the atmospheric boiling point of the reaction mixture.

The present invention also includes a process for the preparation of certain blocked polyisocyanate compounds, i.e., adducts of one or more ketoximes and one or more polyisocyanate compounds, utilizing the process described hereinabove. This embodiment of my invention comprises the steps of:

(1) contacting a ketone having about 5 to 20 carbon atoms with a hydroxylamine salt at a temperature of about 65° to 110° C. in the presence of an alkanol, a heterogenous carbonate base and up to about 5 weight percent, based on the weight of the ketone and alkanol, water to form a ketoxime of the ketone;

(2) adding to the mixture of step (1) sufficient water to obtain a mixture comprising a liquid aqueous phase and a liquid organic phase containing the ketoxime;

(3) separating the organic phase of step (2) and removing substantially all of the alkanol and any water present therein; and (4) reacting the ketoxime with a polyisocyanate compound to obtain the adduct of the ketoxime and the polyisocyanate compound.

The first step of the two-step process is described in detail hereinabove. The purpose of the second step wherein water is added to the reaction mixture resulting from step (1) is the removal of the inorganic salts formed as a result of the ketoxime-forming reaction. The inorganic salts comprise the cation of the heterogenous carbonate base and the anion, e.g., chloride or sulfate, of the hydroxylamine salt and any heterogenous carbonate base not consumed in the reaction of step (1). The amount of water used typically ranges from about 0.5 to 2.0 volumes water per volume of reaction mixture resulting from step (1).

In the third step the ketoxime containing, organic phase is separated from the aqueous phase in which the inorganic salts are dissolved and/or dispersed. All, or substantially all, of the alcohol and water, if any, present in the organic phase then is removed, for example, by distillation under vacuum to obtain a purified organic phase comprising the ketoxime and most of any unreacted ketone present. Preferably, the purified organic phase does not contain any significant amount, e.g., not more than about 5 weight percent, preferably not more than 0.5 weight percent based on the weight of the ketoxime, of any compounds such as water and alkanols which are reactive with the isocyanato group.

The fourth step may be carried out by adding a polyisocyanate compound to the purified, ketoxime-containing, organic phase obtained from step (3). The reaction of the ketoxime and the polyisocyanate compound typically is conducted at a temperature in the range of about 20° to 100° C. The fourth step optionally may include an inert solvent such as a hydrocarbon, e.g., heptane, xylene and toluene; a halogenated hydrocarbon, e.g., methylene chloride and chlorobenzene; an ether, e.g., dioxane and tetrahydrofuran; an alkyl carboxylate ester, e.g., $C_1$–$C_4$ alkyl acetates such as ethyl and butyl acetate; or a mixture of such inert solvents. The fourth step also may be carried out in the presence of a catalyst selected from tertiary amines and organo-tin compounds. Examples of the tertiary amines include trialkyl amines, e.g., having a total carbon content of up to 60 carbon atoms, preferably up to about 12 carbon atoms, and heterocyclic amines such as N alkyl-piperidine, N-alkylmorpholine, 1,4-diazabicyclo[2.2.2]octane, pyridine, N-alkylimidazole and the like. Examples of the organo-tin catalysts include dialkyltin dicarboxylates such as dibutyltin dilaurate and dibutyltin dimaleate, dialkyltin oxides such as dibutyltin oxide, tin carboxylates such as stannous octanoate and dialkanoyloxy tetraalkyl-distanoxanes such as 1,3-diacetoxy-1,1,3,3-tetrabutyldistanoxane.

The polyisocyanate compounds useful in the four step embodiment of my invention include aliphatic, cycloaliphatic and aromatic compounds which contain at least two isocyanato groups and are capable of cross linking coating compositions, e.g., thermosetting coating compositions wherein the polymeric resin or binder contains chain terminating and/or pendant hydroxyl groups. Examples of the polyisocyanate compounds include hexamethylene diisocyanate, isophorone diisocyanate, methylene bis(cyclohexylisocyanate), toluene diisocyanate and bis(1-isocyanato-1-methylethyl)benzene. The preferred diisocyanates comprise methylene bis(cyclohexylisocyanate), bis(1-isocyanato-1-methylethyl)-benzene and isophorone diisocyanate. The material commonly referred to as isophorone diisocyanate may consist primarily of the difunctional, monomeric isophorone diisocyanate, i.e., a mixture of the cis and trans isomers of 3-isocyanatomethyl 3,5,5-trimethylcyclohexylisocyanate, the difunctional dimer thereof, the trifunctional trimer thereof or a mixture of the monomeric, dimeric and/or trimeric forms. For example, the polyisocyanate compound used may be a mixture consisting primarily of the difunctional, monomeric isophorone diisocyanate and the trifunctional trimer of isophorone diisocyanate. The trimer of isophorone di-isocyanate, i.e., mixed isomers of triisocyanato cyclic isocyanurate, is described in U.S. Pat. No. 4,150,211. The preferred ketoxime-polyisocyanate adducts which may be prepared according to the process described herein are comprised of polyisocyanate compounds wherein the isocyanato groups have been converted to groups having the formula

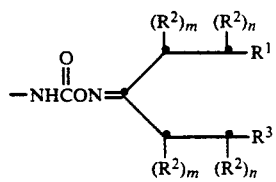

wherein $R^1$, $R^2$, $R^3$, m and n are defined hereinabove. The preferred polyisocyanate compounds consist of the above-described monomeric, dimeric and trimeric forms of isophorone diisocyanate, methylene-bis(4,4'-cyclohexylisocyanate) and 1,3- and 1,4-bis(1-isocyanato-1-methylethyl)benzene.

The processes provided by the present invention are further illustrated by the following examples. Each oximation reaction was monitored by periodically removing samples from the reaction mixture, extracting the mixture with water/methylene chloride and analyzing the resulting organic phase by gas chromatography (GC). Analyses were conducted using a 30 m × 0.25 mm DB-5 capillary column on a Hewlett Packard HP 5890 gas chromatograph equipped with a flame ionization detector, an HP-3393A integrator, and an HP 7673A autoinjector. In each of the following examples the hours of elapsed time (Time) at the time of the removal of each sample is given along with the GC area percents for the ketone reactant (Ketone) employed and the oxime product (Oxime) produced. Elapsed reaction time commenced at the time all reagents were combined unless otherwise noted.

For reactions of isocyanates with oximes, reaction progress was determined by infra-red analysis of the characteristic isocyanate absorption at ca. 2230–2260 $cm^{-1}$.

The 2,6-dimethyl-4-heptanone used in the reactions was obtained by the distillation of a commercial grade of 2,6-dimethyl-4-heptanone, which is a mixture of 2,6-dimethyl-4-heptanone and 4,6-dimethyl-2-heptanone to obtain the 2,6-dimethyl-4 -heptanone isomer in 95–99% purity. The spectral data for 2,6-dimethyl-4-heptanone oxime (DMHO) and 2,4-dimethyl-3-pentanone oxime (DMPO) are listed in Table 1.

EXAMPLE 1

In a 3-neck, 1-L flask equipped with a mechanical stirrer, condenser, nitrogen inlet and thermocouple temperature regulator was placed 2,6-dimethyl-4-heptanone (176.7 g; 1.243 mol), hydroxyl amine sulfate (101.7 g; 0.620 mol, 1.24 equivalents) and ethanol (200 mL). The solution was warmed to 40° C. and sodium carbonate (68.95 g; 0.651 mole; 1.301 equivalents) was added portion-wise. After the addition was complete, the solution was warmed to reflux (approximately 95° C.) and the reaction progress was determined by GC.

| Time | Ketone | Oxime |
|---|---|---|
| 0.75* | 96.4 | 0.4 |
| 2.75 | 93.0 | 3.6 |
| 6.00 | 80.9 | 16.0 |
| 10.00** | 31.6 | 65.5 |
| 25.50 | 12.1 | 85.0 |

*pH = 8
**pH = 9

After 27.0 hours, the reaction mixture was cooled to room temperature, 200 mL water were added and the layers separated. The organic phase was washed with brine, concentrated in vacuo, and distilled to give 139.8 g (72% of theory) 2,6-dimethyl-4-heptanone oxime.

EXAMPLE 2

In a 1-L, 3-neck flask equipped with a mechanical stirrer, condenser, nitrogen inlet and thermocouple temperature regulator was placed 2-propanol (172 mL) hydroxylamine sulfate (93.13 g; 0.568 mol, 1.136 equivalents) and 2,6-dimethyl-4-heptanone (164.14 g (1.154 mol). The solution was vigorously stirred and sodium carbonate (63.2 g; 0.596 moles; 1.193 equivalents) was added. After 1.5 hours, the solution was warmed to reflux (99° C.). The progress of the reaction was as follows:

| Time | Ketone | Oxime |
|---|---|---|
| 0.5 | 97.4 | 0.1 |
| 4.0 | 95.4 | 2.3 |
| 8.5 | 90.3 | 7.6 |
| 23.0 | 13.0 | 85.4 |
| 30.0 | 10.0 | 88.2 |

After 30 hours, the reaction was cooled to room temperature, 150 mL water were added and the layers separated. The organic layer was washed with brine and distilled to give 139.85 g (79% of theory) 2,6-dimethyl-4-heptanone oxime.

EXAMPLE 3

This example illustrates the advantages of inclusion of a minor amount of water in the reaction mixture with 2-propanol solvent.

In a 1-L, 3-neck flask equipped with a mechanical stirrer, condenser, thermocouple temperature regulator and nitrogen inlet was placed 2,6-dimethyl-4-heptanone (163.4 g; 1.149 mol), hydroxylamine sulfate (93.2 g; 0.568 mol, 1.136 equivalents), 2-propanol (172 mL), water (10 mL) and sodium carbonate (63.2 g; 0.596 moles, 1.193 equivalents). The solution was heated to reflux (approximately 97° C.) and the extent of reaction determined by GC.

| Time | Ketone | Oxime |
| --- | --- | --- |
| 1.0 | 73.2 | 19.5 |
| 3.0 | 34.3 | 58.3 |
| 5.0* | 21.9 | 70.9 |
| 7.0 | 16.4 | 76.3 |
| 9.0 | 13.1 | 79.1 |
| 22.0 | 6.0 | 86.8 |

*pH = 9

The reaction mixture was cooled to room temperature after 22 hours and 150 mL water were added and the layers separated. The pH of the aqueous phase was 9. The organic layer was washed with brine and distilled as before to give 157.8 g (88.5% of theory) of 2,6-dimethyl-4-heptanone oxime.

EXAMPLE 4

This example illustrates the preparation of 2,6-dimethyl-4-heptanone oxime and subsequent direct use of the material in the preparation of a blocked isocyanate.

In a 2-L, 3-neck flask equipped with a mechanical stirrer, nitrogen inlet, thermocouple temperature regulator and condenser was placed 2,6-dimethyl-4-heptanone (376.8 g; 2.65 mol), 2-propanol (360 mL) and water (21 mL). The solution was warmed to 50° C. at which point hydroxylamine sulfate (206.86 g; 1.26 mol, 2.52 equivalents) was added. Heating was continued to 70° C. and sodium carbonate (135.6 g; 1.279 moles; 2.559 equivalents) was added. Some effervescence was noted at this point. The solution was heated further to 85° C. and maintained at that temperature for 8 hours, after which time 400 mL water were added and the solution was allowed to cool to room temperature. The resulting two phases were separated and washed as described in the preceding examples, the organic phase was filtered through a small pad of filter aid and the solvent was removed at 30–32 torr. Analysis of the resulting crude product by GC (mass 312.6 g) showed it contained 7.5 area percent ketone reactant and 90.1 area percent oxime product. This crude oxime was dissolved in 150 mL methylene chloride and 5 mL triethyl amine. To this solution was added 1,3-bis(1-isocyanato-1-methylethyl)benzene (184 mL; 0.791 mol) dropwise at such a rate as to keep the temperature below 35° C. The solution was subsequently warmed to 55° C. and maintained at that temperature for 40 minutes at which point infra-red spectroscopy showed no remaining isocyanate. The warm solution was poured into an Erlenmeyer flask and recrystallized from petroleum ether/acetone to yield 356.9 g (81% of theory) of the blocked diisocyanate, the adduct of 2,6-dimethyl-4-heptanone oxime and 1,3-bis-(1-isocyanato-1-methylethyl)benzene.

EXAMPLE 5

In a 1-L, 3-neck flask equipped with a mechanical stirrer, nitrogen inlet, reflux condenser and thermocouple temperature regulator was placed 2,4-dimethyl-3-pentanone (201.5 g, 1.764 mol), ethanol (100 mL) and hydroxylamine hydrochloride (129.2 g; 1.859 mol, 1.859 equivalents). The solution was warmed to 38° C. and sodium carbonate (120.7 g; 1.139 moles; 2.278 equivalents) was added portion wise and subsequently heated further to 70° C. The reaction progress was:

| Time | Ketone | Oxime |
| --- | --- | --- |
| 4.0 | 52.4 | 41.9 |
| 6.0 | 16.6 | 78.9 |

After 6 hours reaction time, the solution (pH=9) was allowed to cool to room temperature, 350 mL water and 100 mL methylene chloride were added and the layers separated. The organic phase was washed with brine, concentrated in vacuo and crystallized from the melt to give 159.9 g (70% of theory) 2,4-dimethyl-3-pentanone oxime.

EXAMPLE 6

In a 300 mL flask equipped with a mechanical stirrer, condenser and temperature regulator were placed 2,6-dimethyl-4-heptanone (28.4 g, 0.20 mole), 34 mL of 2-propanol and 2 mL water. The solution was warmed to 40° C. and hydroxylamine sulfate (19.0 g, 0.116 mole) was added. The suspension of hydroxylamine sulfate was maintained at 40° C. with stirring for 10 minutes after which time 6.1 g of calcium carbonate was added. The pH of the reaction mixture was determined by pH paper to be approximately 4 to 5 prior to the calcium carbonate addition and approximately 6 to 7 after the addition. After 10 minutes additional time, another 6.1 g of calcium carbonate was added. After this second addition, the pH was determined to be 8 to 9. The mixture was maintained at 90° to 97° C. over a total reaction period of 22 hours.

| Time | Ketone | Oxime |
| --- | --- | --- |
| 0.5 | 97.30 | 0.35 |
| 1.0 | 94.14 | 3.51 |
| 2.0 | 86.12 | 11.34 |
| 3.0 | 63.82 | 34.35 |
| 5.0 | 41.92 | 58.08 |
| 7.0 | 25.80 | 72.39 |
| 22.0 | 5.70 | 92.32 |

COMPARATIVE EXAMPLE 1

In a 500-mL, 3-neck flask equipped with a magnetic stirrer, nitrogen inlet, thermometer and reflux condenser was placed 2,6-dimethyl-4-heptanone(100 mL; 79 g; 0.556 mol), water (156 ml) and hydroxylamine sulfate (44.08 g; 0.269 mol; [NH$_2$OH]$_2$H$_2$SO$_4$). The solution was cooled in an ice bath and a solution of sodium hydroxide (24.1 g in 25 mL water) was added dropwise at such a rate as to keep the temperature below 30° C. (approximately 45 minutes). The solution pH after the addition was 13–14. The solution was allowed to warm to room temperature and stirred for 14 hours at that temperature. After this point gas chromatography indicated that the organic phase consisted of 95.9% of the ketone reactant and only 0.9% oxime product. The solution was warmed to and maintained at 78°–90° C. and the progress of the reaction was determined by GC.

| Time | Ketone | Oxime |
|---|---|---|
| 22.0 | 84.5 | 12.0 |
| 31.0 | 75.1 | 21.2 |
| 42.0 | 63.2 | 33.2 |
| 46.0 | 59.9 | 37.0 |
| 51.5 | 51.5 | 45.3 |
| 74.0 | 32.6 | 64.0 |
| 125.5 | 23.3 | 73.1 |
| 137.5 | 23.2 | 73.4 |

After 137.5 hours, the solution was cooled to room temperature, the layers were separated and the organic phase washed with brine. The organic layer was concentrated in vacuo and vacuum distilled at 85° C./1 torr to give 45.35 g (54% of theory) of 2,6-dimethyl-4-heptanone oxime.

This example illustrates the extremely poor reaction rate when 2,6-dimethyl-4-heptanone oxime is prepared in aqueous reaction medium using sodium hydroxide according to known procedures.

COMPARATIVE EXAMPLE 2

In a 500-mL, 3-neck flask equipped with a mechanical stirrer, addition funnel, and thermocouple-regulated heating mantle was placed 2,6-dimethyl-4-heptanone (89.2 g; 0.627 mol), ethanol (25 mL) and a solution of hydroxylamine sulfate (52 g; 0.317 mol, 0.634 equivalents) in water (79 mL). The solution was stirred and a solution of sodium hydroxide (25.8 g; 0.645 moles) in water (30 mL) was added drop-wise at such a rate as to keep the temperature below 46° (approximately 30 minutes). The solution was heated to reflux (99° C.) after addition of the sodium hydroxide solution and the reaction progress determined.

| Time | Ketone | Oxime |
|---|---|---|
| 0.25 | 95.8 | 0.1 |
| 2.0 | 94.6 | 1.6 |
| 4.5 | 88.5 | 7.8 |
| 8.5 | 76.5 | 19.5 |
| 23.0 | 32.3 | 64.1 |
| 27.0 | 26.0 | 70.5 |

After 28 hours, the crude reaction mixture was cooled to room temperature and the reaction mixture worked-up as described in the preceding example to give 71.1 g (72.2% of theory) 2,6-dimethyl-4-heptanone.

COMPARATIVE EXAMPLE 3

This example describes the preparation of the oxime of 2,6-dimethyl-4-heptanone according to the procedure described in Example 2 of U.S. Pat. No. 4,128,580. In a 300 mL flask equipped with a magnetic stirrer, condenser and temperature regulator was placed 2,6-dimethyl-4-heptanone (14.2 g, 0.10 mole) and 29.5 mL of 1,2-dichloroethane. The solution was warmed to 40° C. and a solution of hydroxylamine sulfate (9.5 g, 0.058 mole) in 20 mL water was added. The solution was maintained at 40° C. with stirring for 60 minutes after which time 2.5 g of calcium carbonate was added. The pH of the reaction mixture was determined by pH paper to be approximately 1 to 2 prior to the calcium carbonate addition and approximately 4 to 5 after the addition. After 30 minutes additional time, another 2.5 g of calcium carbonate was added. The mixture was maintained at 40° C. over a total reaction period of 23.5 hours.

| Time | Ketone | Oxime |
|---|---|---|
| 0.25 | 100 | — |
| 1.00* | 97.8 | — |
| 1.33 | 98.1 | 0.03 |
| 1.75** | 97.8 | 0.07 |
| 2.33 | 97.9 | 0.15 |
| 3.25*** | 97.6 | 0.29 |
| 4.50 | 97.4 | 0.49 |
| 6.50 | 97.0 | 0.78 |
| 8.00 | 96.7 | 1.06 |
| 23.50 | 95.7 | 2.03 |

*Prior to addition of calcium carbonate
**After addition of second portion of calcium carbonate
***pH = 4–5

COMPARATIVE EXAMPLE 4

The procedure of Comparative Example 3 was repeated except that after the addition of the second portion of calcium carbonate, the reaction mixture was warmed to and maintained at reflux over the remainder of the reaction time.

| Time | Ketone | Oxime |
|---|---|---|
| 0.25 | 98.05 | 0.04 |
| 1.00* | 97.65 | 0.36 |
| 2.00 | 96.34 | 1.42 |
| 3.00** | 95.30 | 2.43 |
| 4.00 | 94.44 | 3.25 |
| 6.50 | 92.53 | 5.18 |
| 8.00 | 91.56 | 6.13 |
| 23.50 | 85.90 | 11.69 |

*Prior to addition of calcium carbonate
**After addition of second portion of calcium carbonate

TABLE I $^1$H NMR Data for DMHO and DMPO

| DMHO(δ, (m, #H's)) | DMPO(δ, (m, #H's)) |
|---|---|
| 0.91(d, 6H) | 1.13(d, 6H) |
| 0.94(d, 6H) | 1.18(d, 6H) |
| 1.82–1.95(m, 1H) | 2.50–2.64(m, 1H) |
| 1.96–2.04(m, 1H) | 3.12–3.28(m, 1H) |
| 2.04(d, 2H) | |
| 2.24(d, 2H) | |

The invention has been described in detail with particular reference to preferred embodiments thereof. However, it will be understood that variations and modifications may be effected within the spirit and scope of the invention.

I claim:

1. Process for the preparation of a ketoxime which comprises contacting a ketone having about 5 to 20 carbon atoms with a hydroxylamine salt at a temperature of about 65° to 110° C. in the presence of an alkanol, a heterogeneous carbonate base and up to about 5 weight percent, based on the weight of the ketone and alkanol, water.

2. Process according to claim 1 for the preparation of an oxime of an alkanone of about 5 to 20 carbon atoms which comprises reacting an alkanone of 5 to 20 carbon atoms with a hydroxylamine salt at a temperature of about 65° to 110° C. in the presence of an alkanol of up to about 4 carbon atoms, a heterogeneous carbonate base selected from the carbonates and bicarbonates of the alkali and alkaline earth metals, and up to about 5 weight percent, based on the weight of the alkanone and alkanol, water.

3. Process according to claim 2 wherein the process is carried out in the presence of up to about 3 to 5 weight percent water based on the weight of the alkanone and alkanol.

4. Process according to claim 2 wherein the hydroxylamine salt is hydroxylamine hydrochloride or hydroxylamine sulfate, the heterogeneous carbonate base is a carbonate of an alkali metal and the process is carried out in the presence of about 3 to 5 weight percent water based on the weight of the alkanone and alkanol.

5. Process for the preparation of an oxime of a branched chain ketone having the formula

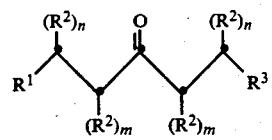

wherein $R^1$ and $R^3$ are independently selected from hydrogen and alkyl of up to about 6 carbon atoms; each $R^2$ is hydrogen or alkyl of up to about 3 carbon atoms; m and n each is 0 or 1; and the sum of $m+n=2$ which comprises reacting said ketone with a hydroxylamine salt at a temperature of about 65° to 100° C. in the presence of an alkanol, a heterogeneous carbonate base and up to about 5 weight percent, based on the weight of the ketone and alkanol, water.

6. Process according to claim 5 which comprises reacting the ketone with a hydroxylamine salt at a temperature of about 65° to 100° C. in the presence of an alkanol of up to about 4 carbon atoms, a heterogeneous carbonate base selected from the carbonates and bicarbonates of the alkali and alkaline earth metals, and up to about 5 weight percent, based on the weight of the ketone and alkanol, water.

7. Process according to claim 6 wherein the process is carried out in the presence of about 3 to 5 weight percent water based on the weight of the ketone and alkanol.

8. Process according to claim 6 wherein the hydroxylamine salt is hydroxylamine hydrochloride or hydroxylamine sulfate, the heterogeneous carbonate base is a carbonate of an alkali metal and the process is carried out in the presence of about 3 to 5 weight percent water based on the weight of the ketone and alkanol.

9. Process for the preparation of the oxime of 2,4-dimethyl-3-pentanone or 2,6-dimethyl-4-heptanone which comprises reacting 2,4-dimethyl-3-pentanone or 2,6-dimethyl-4-heptanone with a hydroxylamine salt in the presence of an alkanol of up to about 4 carbon atoms, a heterogeneous carbonate base selected from the carbonates and bicarbonates of the alkali and alkaline earth metals, and up to about 5 weight percent, based on the weight of the ketone and alkanol, water.

10. Process according to claim 9 wherein the process is carried out in the presence of about 3 to 5 weight percent water based on the weight of the alkanol and the 2,4-dimethyl-3-pentanone or 2,6-dimethyl-4-heptanone.

11. Process according to claim 9 wherein the hydroxylamine salt is hydroxylamine hydrochloride or hydroxylamine sulfate, the heterogeneous carbonate base is a carbonate of an alkali metal and the process is carried out in the presence of about 3 to 5 weight percent water based on the weight of the alkanol and the 2,4-dimethyl-3-pentanone or 2,6-dimethyl-4-heptanone.

12. Process for the preparation of the oxime of 2,4-dimethyl-3-pentanone or 2,6-dimethyl-4-heptanone which comprises reacting at a temperature of about 65° to 110° C. 2,4-dimethyl-3-pentanone or 2,6-dimethyl-4-heptanone with hydroxylamine hydrochloride or sulfate in the presence of an alkanol selected from ethanol, 1-propanol, 2-propanol or a mixture thereof, sodium or potassium carbonate, and up to about 5 weight percent, based on the weight of the alkanol and the 2,4-dimethyl-3-pentanone or 2,6-dimethyl-4-heptanone, water.

13. Process for the preparation of an adduct of a ketoxime and a polyisocyanate compound which comprises the steps of:
  (1) contacting a ketone having about 5 to 20 carbon atoms with a hydroxylamine salt at a temperature of about 65° to 110° C. in the presence of an alkanol, a heterogenous carbonate base and up to about 5 weight percent, based on the weight of the ketone and alkanol, water to form a ketoxime of the ketone;
  (2) adding to the mixture of step (1) sufficient water to obtain a mixture comprising a liquid aqueous phase and a liquid organic phase containing the ketoxime;
  (3) separating the organic phase of step (2) and removing substantially all of the alkanol and any water present therein; and
  (4) reacting the ketoxime with a polyisocyanate compound to obtain the adduct of the ketoxime and the polyisocyanate compound.

14. Process according to claim 13 for the preparation of an adduct of a branched chain ketoxime and a polyisocyanate compound which comprises the steps of:
(1) contacting a ketone having the formula

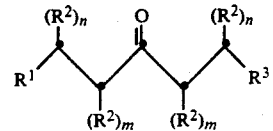

wherein $R^1$ and $R^3$ are independently selected from hydrogen and alkyl of up to about 6 carbon atoms; each $R^2$ is hydrogen or alkyl of up to about 3 carbon atoms; m and n each is 0 or 1; and the sum of $m+n=2$ which comprises reacting said ketone with a hydroxylamine salt at a temperature of about 65° to 110° C. in the presence of an alkanol, a heterogeneous carbonate and up to about 5 weight percent, based on the weight of the ketone and alkanol, water to form an oxime of the ketone;
  (2) adding to the mixture of step (1) sufficient water to obtain a mixture comprising a liquid aqueous phase and a liquid organic phase containing the oxime of the ketone;
  (3) separating the organic phase of step (2) and removing substantially all of the alkanol and any water present therein; and
  (4) reacting the oxime of the ketone with a polyisocyanate compound selected from isophorone diisocyanate, methylene bis(4,4'-cyclohexylisocyanate) and 1,3- and 1,4-bis(1-isocyanato-1-methylethyl)benzene.

15. Process according to claim 14 wherein step (1) is carried out in the presence of about 3 to 5 weight percent water based on the weight of the ketone and alkanol, the hydroxylamine salt is hydroxylamine hydrochloride or hydroxylamine sulfate and the heterogeneous carbonate base is a carbonate of an alkali metal.

* * * * *